United States Patent
Bartoli et al.

(10) Patent No.: US 7,205,287 B2
(45) Date of Patent: Apr. 17, 2007

(54) PLATINUM COMPLEXES HAVING ANTITUMOR ACTIVITY

(75) Inventors: Enzo Bartoli, Reggio Emilia (IT); Beniamino Palmieri, Modena (IT); Alessandro Medici, Bologna (IT)

(73) Assignee: ICE s.r.l., Reggio Emilia (IT)

( * ) Notice: Subject to any disclaimer, the term of this patent is extended or adjusted under 35 U.S.C. 154(b) by 258 days.

(21) Appl. No.: 10/971,900

(22) Filed: Oct. 22, 2004

(65) Prior Publication Data

US 2005/0107337 A1 May 19, 2005

(51) Int. Cl.
*A61K 31/575* (2006.01)
*C07J 51/00* (2006.01)
(52) U.S. Cl. .................................... 514/177; 552/506
(58) Field of Classification Search ................ 552/506; 514/177

See application file for complete search history.

*Primary Examiner*—Barbara P. Badio
(74) *Attorney, Agent, or Firm*—Walter H. Schneider

(57) ABSTRACT

A platinum complex having antitumor activity in which the metal ligands are dehydrocholic acid and phosphine.

2 Claims, No Drawings

PLATINUM COMPLEXES HAVING ANTITUMOR ACTIVITY

FIELD OF THE INVENTION

The present invention relates to platinum (II) complexes having antitumor activity, in particular complexes in which the metal is coordinated by a phosphine and dehydrocholic acid.

TECHNOLOGICAL BACKGROUND

From the discovery of cisplatin antitumor properties [B. Rosenberg et al., Nature 205, 698, 1965; 222, 385 (1972)], a number of searches have been focused on the development of platinum complexes having lower toxicity and higher selectivity towards the tumour cells. cis-Platinum is in fact, despite its nephrotoxicity and ototoxicity, particularly effective when used in combined chemotherapies in the treatment of the tumors of testes, ovary, head and neck.

Platinum complexes in which two coordination sites are occupied by amino ligands, whereas the two other coordination sites are occupied by functional groups of a steroid derivative have been described.

DETAILED DISCLOSURE OF THE INVENTION

The present invention relates to platinum (II) complexes with antitumor activity in which the metal is coordinated by dehydrocholic acid and a phosphine, in particular the complex cis-[dehydrocholate bis(triphenylphosphine)-platinum (II)] of formula (1):

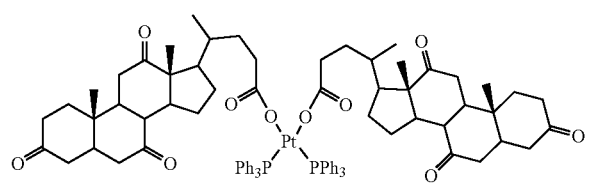

1

Compound (1) is obtained by reacting silver dehydrocholate (2), in turn obtained by treatment of dehydrocholic acid (3) with silver oxide, with cis-[PtCl$_2$(PPh$_3$)$_2$] according to the following scheme:

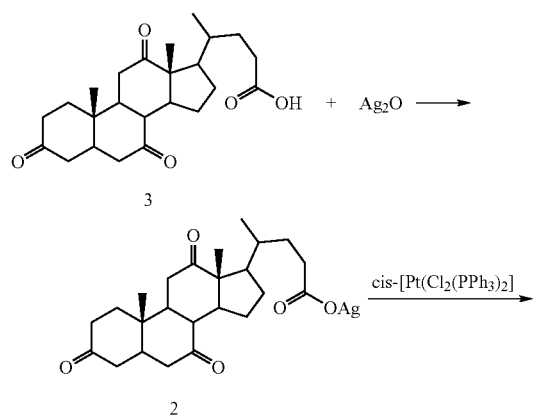

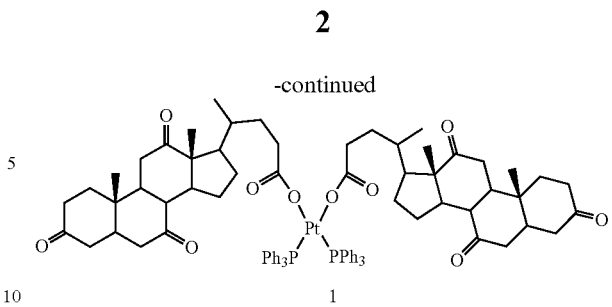

1

Typically, the reaction between dehydrocholic acid and silver oxide is carried out in water, heating under reflux until disappearance of the silver oxide dark residue.

The reaction between the silver salt (2) and the cis-[PtCl$_2$(PPh$_3$)$_2$] complex is preferably carried out dissolving the cis-[PtCl$_2$(PPh$_3$)$_2$] complex in methylene chloride and suspending the silver salt until complete precipitation of Ag$_2$O, which is removed from the reaction mixture by centrifugation, filtration and optionally by treatment with active charcoal. Alternatively, the reaction can be carried out in solvents in which both salt (2) and cis-[PtCl$_2$(PPh$_3$)$_2$] complex are insoluble, preferably acetone and ethyl acetate, and in which compound (1) is soluble.

The cis-[PtCl$_2$(PPh$_3$)$_2$] complex is obtained according to what described in Mc Dermott J. X., White J. F., Whitesides M. J. Am. Chem. Soc. 1976, 98, 5621, by reacting cis-[PtCl$_2$(1.5-cyclooctadiene)] with triphenylphosphine in methylene chloride, or according to what described in Bailar John C. Jr, Ilatani H. Inorganic Chemistry, vol. 4, n. 11, 1965, by reacting K$_2$PtCl$_4$ with triphenylphosphine in ethanol.

Compound (1), when administered to humans or animals bearing tumors which can be treated with cisplatin or are resistant to cisplatin, are capable of inducing the regression of said tumors.

Compound (1) can be used for the treatment of those pathological conditions for which cisplatin is used, in particular for the treatment of tumors [Douple et al. Cisplatin Current Status and Developments, Ed. A. W. Prestayk et al., Academic Press, 125 (1980; Douple et al. Platinum Metals Res., 29; 118 (1985)].

Therefore, the present invention also relates to pharmaceutical compositions containing a therapeutically effective amount of compound (1) in mixture with conventional carriers and excipients.

The effective dose of compound (1) will be determined by the expert physician according to conventional methods. The relationship between the dosages used for animals of various species and size and those for the humans (based on mg/m$^2$ body area) is described by Freirech et al., Quantitative Comparison of Toxicity of Anticancer Agents in Mouse, Rat, Hamster, Dog, Monkey and Man Cancer Chemother. Rep, 50, n. 4, 219–244 (1986). The patient will receive doses of the complex ranging from 0.1 to 200 mg/kg body weight, with a dosage regimen which will vary depending on a number of factors, well known to the skilled clinician, and the treatment regimen will vary depending on the type of tumor to treat and the conditions of the patient.

Compound (1) can be administered through the oral, parenteral, topical or intratumoral routes.

The pharmaceutical compositions for the parenteral administration comprise saline sterile solutions or suspensions or sterile powders for the extemporaneous preparation of solutions or suspensions. The pharmaceutical compositions for the parenteral administration also comprise oily preparations for the intramuscular or intraperitoneal administration.

The pharmaceutical compositions for the oral administration comprise, for example, syrups or similar liquid forms, as well as solid forms such as tablets, capsules and the like.

The pharmaceutical compositions according to the present invention are prepared following conventional methods, such as those reported in Remington's Pharmaceutical Sciences Handbook, XVII Ed., Mack Pub., N.Y., U.S.A.

Compound (1) may be administered together with one or more agents which enhance their antitumor activity or which alleviate the side effects accompanying platinum complexes therapy, for example together with reduced glutathione, as disclosed in GB 2.174.905 and in U.S. Pat. No. 4,871,528.

Complex (1) can also be advantageously administered together with other platinum complexes having antitumor activity, therefore a further object of the present invention are pharmaceutical compositions containing compound (1) in combination with a platinum complex with antitumor activity.

The present invention further relates to the use of compound (1) for the preparation of pharmaceutical compositions for the treatment of mammals affected with tumors which can be treated with cis-platinum or are resistant to cis-platinum.

The invention is illustrated in greater detail by the following example.

EXAMPLE

Materials and Methods $^1$H-NMR spectra were recorded with a Varian Gemini spectrometer 300 MHz at the frequency of 300 MHz. Chemical shifts are expressed in ppm.

$^{13}$C-NMR spectrum of triacid (11a) was recorded with a Varian Gemini spectrometer 300 MHz at the frequency of 75.1 MHz. Chemical shifts are expressed in ppm.

Infrared spectra were recorded in KBr with a NICOLET 510P Fourier transformed spectrophotometer.

Preparation 1

Synthesis of cis-[PtCl$_2$(PPh$_3$)]

Method 1 a) Cis-[PtCl$_2$(1,5-cyclooctadiene)]

5 g of K$_2$PtCl$_4$ (12 mmoles) are dissolved in 80 ml of water and 80 ml of glacial acetic acid. The resulting red solution is added with 6 ml (48 mols) of 1,5-cyclooctadiene and refluxed for 70–80 minutes, during which time a solution of a white gummy solid in a pale yellow liquid forms. The solution is concentrated to small volume under reduced pressure and filtered through a porous septum. The product is washed with water on the filter, then dried to constant weight, then washed again with n-hexane to remove cyclooctadiene residues. 4.1 g (10.95 mmoles) of product as a white solid are obtained (yield: 91%).

b) cis-[PtCl$_2$(PPh$_3$)$_2$]

A solution of 2.6 g (7 mmoles) of cis-[PtCl$_2$(1,5-cyclooctadiene)] in 80 ml of CH$_2$Cl$_2$ is added, drop by drop, with a solution of 3.7 g (14 mmoles) of PPh$_3$ dissolved in 100 ml of CH$_2$Cl$_2$.

Ten minutes after the end of the addition, the solvent is evaporated off under reduced pressure, the residue is washed with n-hexane and filtered through a porous septum.

5 g (6.3 mmoles) of product as a white solid are obtained (yield: 90%).

Method 2

A solution of 5 g (19.3 mmoles) of PPh$_3$ in 60 ml of hot ethanol is refluxed. A solution of 4 g (9.64 mmoles) of K$_2$PtCl$_4$ in 50 ml of water is dropped therein and the mixture is kept under stirring at a temperature of 60° C. for two hours.

The precipitated complex is filtered through a porous septum while hot, washed with water, with hot ethanol and dried over P$_2$O$_5$.

6.85 g (8.66 mmoles) of a white solid are obtained (yield: 90%).

Preparation 2

A solution of 5 g (29.4 mmoles) of AgNO$_3$ in about 30 ml of water, shielded from light, is slowly added with a solution of 1.9 g (33.8 mmoles) of KOH in 20 ml of water, under stirring. Ag$_2$O immediately precipitates as a black, flaky solid. After stirring for some minutes, the mixture is filtered under vacuum through a porous septum. The precipitate is repeatedly washed with water and methanol, then dried to constant weight.

Yield: 3.2 g (13.8 mmoles), 94%.

Preparation 3

Synthesis of Silver Dehydrocholate

A suspension of 3.2 g (13.8 mmoles) of Ag$_2$O and 12.75 g (31.7 mmoles) of dehydrocholic acid (1:2.3 ratio) in about 250 ml of water is refluxed under strong stirring until disappearance of the Ag$_2$O dark residue (5–6 hours with efficient stirring). The mixture is cooled on ice bath and filtered and the precipitate is repeatedly washed with water and acetone, dried to constant weight and optionally washed with CHCl$_3$ to remove any dehydrocholic acid excess.

13.8 g (27.1 mmoles) of silver dehydrocholate as a beige solid are obtained.

Yield: 86%.

Preparation 4 cis-[(PPh$_3$)$_2$Pt(RCOO)$_2$] Dehydrophosphoplatinum 6.4 g (12.6 mmoles) of silver dehydrocholate are suspended in a solution of 5 g of (6.3 mmoles) of cis-[PtCl$_2$(PPb$_3$)$_2$] in 400 ml of CH$_2$Cl$_2$ and the mixture is stirred overnight, shielding from light.

The precipitated AgCl is removed by centrifugation and repeated filtration through celite on a porous septum to obtain a clear solution (if filtration is insufficient to obtain a clear solution, decolorize with active charcoal). The solvent is evaporated off under reduced pressure and the product is obtained as a white solid.

Yield: 50–70%. $^{31}$P-NMR (CDCl$_3$): 6.6 ($^1J_{PPt}$ 3813) $^1$H-NMR (CDCl$_3$): 0.68 (6H, d, 21-CH$_3$); 0.95 (6H, s, CH$_3$); 1.36 (6H, s, CH$_3$); 1.43–2.35 (48H, m, aliphatic CH, CH$_2$); 2.8 (6H, m, CH vicinal to CO), 7–7.6 (60H, m, aromatic CH). FT-IR (cm$^{-1}$) 1771 (s, v CO); 1629 (m); 1435 (m); 1332 (m); 1098 (m); 693 (s); 529 (s). Elemental analysis (calculated for C$_{84}$H$_{96}$O$_{10}$P$_2$Pt) Calculated: C 66.2%, H 6.3% Found: C 62.8%, H 5.9%

The invention claimed is:
1. A compound of formula (1):
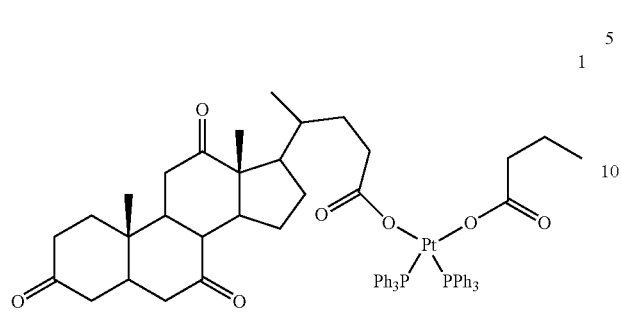
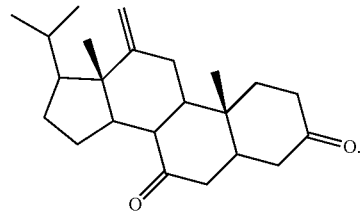
2. Pharmaceutical compositions containing the compound of formula (1)
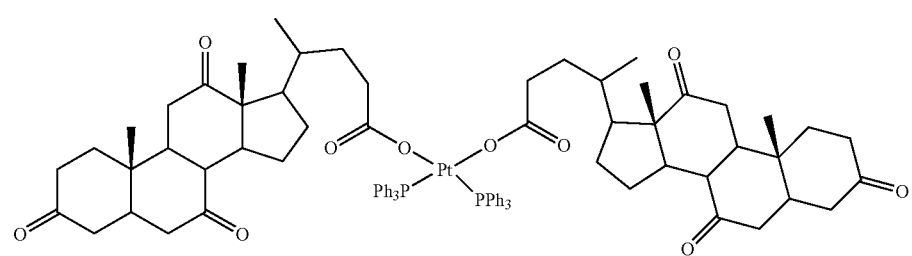
in mixture with suitable excipients and/or carriers.
* * * * *